United States Patent [19]

Stegelmeier et al.

[11] Patent Number: 4,515,801
[45] Date of Patent: May 7, 1985

[54] FUNGICIDALLY ACTIVE PYRANO-PYRAZOLE DERIVATIVES

[75] Inventors: Hartmut Stegelmeier, Hilden; Wilhelm Brandes, Leichlingen, both of Fed. Rep. of Germany

[73] Assignee: Bayer Aktiengesellschaft, Leverkusen, Fed. Rep. of Germany

[21] Appl. No.: 550,076

[22] Filed: Nov. 8, 1983

[30] Foreign Application Priority Data

Nov. 26, 1982 [DE] Fed. Rep. of Germany ....... 3243714

[51] Int. Cl.$^3$ .................... A01N 43/90; C07D 487/02
[52] U.S. Cl. ...................................... 514/403; 548/370
[58] Field of Search ...................... 548/370; 424/273 P

[56] References Cited

FOREIGN PATENT DOCUMENTS 0001428 4/1979 European Pat. Off. .
2521568 8/1983 France ............................ 424/273 N

OTHER PUBLICATIONS

Angew. Chem. Int. Ed. Engl., vol. 21, No. 11 (1982), pp. 863–864, Lutz-F. Tietze et al., "Control of the Conformation of Transition States in Intramolecular Diels-Alder Reactions with Inverse Electron Demand".

Primary Examiner—Henry R. Jiles
Assistant Examiner—Kurt G. Briscoe
Attorney, Agent, or Firm—Sprung Horn Kramer & Woods

[57] ABSTRACT

Pyrano-pyrazole derivative of the formula

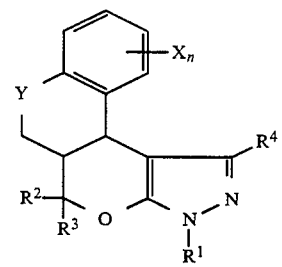

in which
$R^1$ represents hydrogen, alkyl, alkanoyl, alkoxycarbonyl, optionally substituted phenyl or optionally substituted phenylalkyl,
$R^2$ and $R^3$ can be identical or different and represent hydrogen, alkyl or optionally substituted phenyl,
$R^4$ represents cyano, alkyl, alkoxycarbonyl or optionally substituted phenyl,
Y represents oxygen, sulphur or the methylene group,
X represents halogen, alkyl, alkoxy, alkylthio, halogenoalkyl, dialkylamino, nitro or cyano and n represents a number from 0 to 3, which possess fungicidal activity.

10 Claims, No Drawings

FUNGICIDALLY ACTIVE PYRANO-PYRAZOLE DERIVATIVES

The invention relates to new pyrano-pyrazole derivatives, a process for their preparation and their use as agents for combating pests.

It is already known that, in addition to a number of other classes of substances, certain heterocyclic compounds, such as, for example, N-trichloromethylthiotetrahydrophthalimide, also have fungicidal properties (compare R. Wegler, "Chemie der Pflanzenschutz- und Sch/ädlingsbek/ämpfungsmittel" ("Chemistry of Plant Protection and Pest-Combating Agents") Volume 2, page 108, Springer Verlag Berlin/Heidelberg/New York 1970).

However, the activity of these compounds is not always completely satisfactory, especially when low amounts and concentrations are applied.

New pyrano-pyrazole derivatives of the general formula (I)

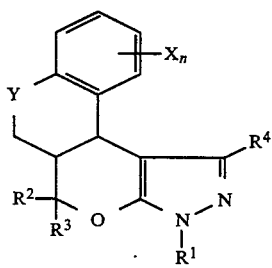

in which $R^1$ represents hydrogen, alkyl, alkanoyl, alkoxycarbonyl, optionally substituted phenyl or optionally substitued phenylalkyl, $R^2$ and $R^3$ can be identical or different and represent hydrogen, alkyl or optiionaly substituted phenyl, $R^4$ represents cyano, alkyl, alkoxycarbonyl or optionally substituted phenyl, Y represents oxygen, sulphur or the methylene group, X represents halogen, alkyl, alkoxy, alkylthio, halogenoalkyl, dialkylamino, nitro or cyano and n represents a number from 0 to 3, have been found.

It has furthermore been found that the new pyrano-pyrazole derivatives of the general formula (I)

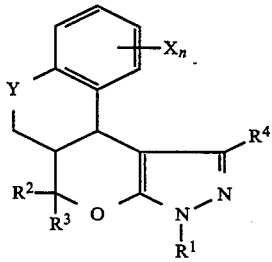

in which $R^1$ represents hydrogen, alkyl, alkanoyl, alkoxycarbonyl, optionally substituted phenyl or optionally substituted phenylalkyl, $R^2$ and $R^3$ can be identical or different and represent hydrogen, alkyl or optionally substituted phenyl, $R^4$ represents cyano, alkyl, alkoxycarbonyl or optionally substituted phenyl, Y represents oxygen, sulphur or the methylene group, X represents halogen, alkyl, alkoxy, alkylthio, halogenoalkyl, dialkylamino, nitro or cyano and n represents a number from 0 to 3, are obtained by a process in which substituted aromatic aldehydes of the general formula (II)

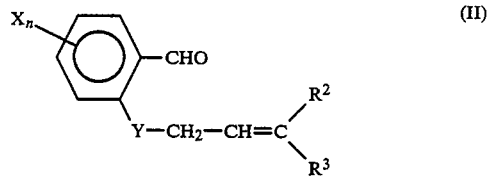

in which $R^2$, $R^3$, X, Y and n have the abovementioned meaning, are reacted with pyrazolinones of the general formula (III)

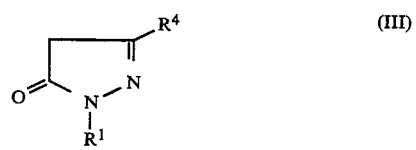

in which $R^1$ and $R^4$ have the abovementioned meaning, in the presence of a diluent and if appropriate in the presence of a catalyst.

The new pyrano-pyrazole derivatives of the general formula (I) have powerful fungicidal properties. Surprisingly, the compounds of the formula (I) according to the invention have a better fungicidal activity than the compound N-trichloromethylthio-tetrahydrophthalimide, which is known from the prior art and is a closely related compound from the point of view of its action.

The substances according to the invention thus represent an enrichment of the art.

Formula (I) provides a general definition of the pyrano-pyrazole derivatives according to the invention.

Particularly preferred compounds of the formula (I) are those in which $R^1$ represents hydrogen, straight-chain or branched alkyl, alkanoyl or alkoxycarbonyl with in each case up to 4 carbon atoms in the alkyl part, phenyl which is optionally monosubstituted or polysubstituted by identical or different substituents or phenylalkyl which has 1 or 2 carbon atoms in the alkyl part and is optionally monosubstituted or polysubstituted by identical or different substituents, possible substituents on the phenyl in each case being: halogen, cyano, nitro, alkyl with up to 4 carbon atoms, alkoxy, alkylthio and dialkylamino with 1 or 2 carbon atoms in the particular alkyl parts, and halogenoalkyl with 1 or 2 carbon atoms and up to 5 identical or different halogen atoms, $R^2$ and $R^3$, which can be identical or different, represent hydrogen, straight-chain or branched alkyl with up to 4 carbon atoms or phenyl which is optionally monosubstituted or polysubstituted by identical or different substituents from the group comprising halogen and alkyl with up to 4 carbon atoms, R⁴ represents straight-chain or branched alkyl or alkoxycarbonyl with in each case up to 4 carbon atoms in the alkyl part, cyano or phenyl which is optionally monosubstituted or polysubstituted by identical or different substituents from the group comprising halogen and alkyl with up to 4 carbon atoms, Y represents oxygen, sulphur or the methylene grouping, X represents halogen, cyano, nitro, straight-chain or branched alkyl with up to 4 carbon atoms, alkoxy, alkylthio or dialkylamino with 1 or 2 carbon atoms in the particular alkyl parts or halogenoalkyl with 1 or 2 carbon atoms and up to 5 identical or different halogen atoms and n represents a number from 0 to 3.

Very particularly preferred compounds of the formula (I) are those in which

R¹ represents hydrogen, methyl, ethyl or n- or i-propyl, acetyl, methoxycarbonyl or ethoxycarbonyl, or phenyl, benzyl or phenethyl which is optionally mono-, di- or tri-substituted by identical or different substituents, especially suitable substituents on the particular phenyl being: fluorine, chlorine, bromine, cyano, nitro, methyl, methoxy, methylthio, dimethylamino and trifluoromethyl, R² and R³, which can be identical or different, represent hydrogen, methyl, or phenyl which is optionally mono-, di- or tri-substituted by identical or different substituents from the group comprising chlorine and methyl, R⁴ represents methyl, ethyl, n- or i-propyl, t-butyl, cyano, methoxycarbonyl, ethoxycarbonyl or phenyl which is optionally mono-, di- or trisubstituted by identical or different substituents from the group comprising chlorine and methyl, Y represents oxygen, sulphur or the methylene grouping, X represents fluorine, chlorine, bromine, cyano, nitro, methyl, methoxy, methylthio, dimethylamino or trifluoromethyl and n represents a number from 0 to 2.

The following compounds of the general formula (I) may be mentioned specifically, in addition to the compounds mentioned in the preparation examples:

(I)

| R¹ | R² | R³ | R⁴ | X | Y | n |
|---|---|---|---|---|---|---|
| H | CH₃ | CH₃ | CN | — | O | 0 |
| H | CH₃ | CH₃ | CH₃ | — | —CH₂— | 0 |
| H | CH₃ | CH₃ | CH₃ | 8,11-Cl₂ | S | 2 |
| CH₃OCO | CH₃ | CH₃ | CH₃ | — | O | 0 |
| C₂H₅OCO | CH₃ | CH₃ | CH₃ | — | O | 0 |
| C₂H₅OCO | CH₃ | CH₃ | CH₃ | — | S | 0 |
| H | CH₃ | CH₃ | CH₃ | 10-NO₂ | —CH₂— | 1 |
| H | CH₃ | CH₃ | CH₃ | 8,11-Cl₂ | —CH₂— | 2 |

If, for example, 2-(3-methyl-2-butenyloxy)-benzaldehyde and 3-methyl-pyrazolin-5-one are used as starting substances, the course of the reaction in the process according to the invention can be represented by the following equation:

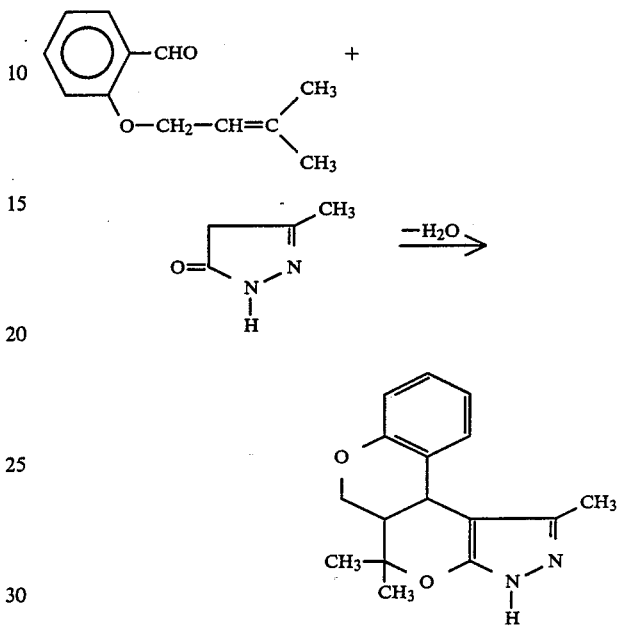

Formula (II) provides a general definition of the substituted aromatic aldehydes required for carrying out the process according to the invention.

The substituted aromatic aldehydes of the formula (II) are known [compare, for example: Chem. Pharm. Bull. 27, 2943 (1979), Belgian Pat. No. 816,463 or Liebigs Ann. Chem. 401, 21 (1913)].

Formula (III) provides a general definition of the pyrazolinones also required for carrying out the process according to the invention.

The pyrazolinones of the formula (III) are likewise known (compare, for example, "The Chemistry of Heterocyclic Compounds" Volume 20, Wiley, New York (1964).

Possible diluents for the process according to the invention are inert organic solvents. These include, preferably, aromatic hydrocarbons, such as, for example, benzene, toluene, xylene or tetralin.

The reaction according to the invention can be carried out in the presence of a catalyst. It is possible to employ all the acid and, in particular, basic catalysts which can customarily be used. Particularly preferred catalysts include organic nitrogen bases, such as, for example, piperidine, pyridine, morpholine and triethylamine.

The reaction temperatures can be varied within a substantial range in the process according to the invention. In general, the reaction is carried out at temperatures between 80° C. and 200° C., preferably at the boiling point of the solvent used.

In carrying out the process according to the invention, 1.0 to 1.3 mols, preferably 1.1 to 1.2 mols, of the substituted aromatic aldehyde of the formula (II) are generally employed per mol of pyrazolinone of the formula (III).

The starting compounds are heated together with 1 to 3 g of the catalyst in the particular diluent over a water separator, until the amount of water separated off remains constant.

To isolate the compounds of the formula (I), the cooled reaction mixture is filtered and, if necessary, the solid thus obtained is recrystallized from a suitable solvent.

The active compounds according to the invention exhibit a powerful microbicidal action and can be employed in practice for combating undesired microorganisms. The active compounds are suitable for use as plant protection agents.

Fungicidal agents are thus employed, for example, in plant protection for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Botrytis species, such as, for example, against the gray mold causative organism (*Botrytis cinerea*). In addition, they can also be used for combating rice diseases, such as, for example, *Pellicularia sasakii*.

The active compounds can be converted to the customary formulations, such as solutions, emulsions, wettable powders, suspensions, powders, dusting agents, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

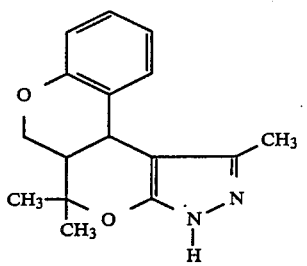

29.4 g (0.3 mol) of 3-methylpyrazolin-5-one and 62.7 g (0.33 mol) of 2-(3-methyl-2-butenyloxy)-benzaldehyde are boiled under reflux together with 1 ml of piperidine in 600 ml of absolute toluene for 15 hours, using a water separator. When the reaction has ended, the mixture is cooled in an ice-bath and the crystals which have precipitated are filtered off with suction. The crude product is recrystallized from ethanol. After drying, 51.4 g (63% of theory) of 1,5,5-trimethyl-5a,11b-dihydro-3H,5H,6H,4,7-dioxa-2,3-diazacyclopenta-[c]-phenanthrene of melting point 271° C. are obtained.

PREPARATION OF THE STARTING MATERIAL

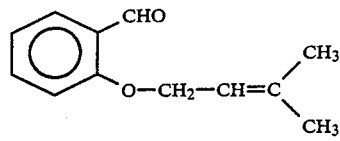

244 g (2 mols) of salicylaldehyde in 400 ml of dimethylformamide are added dropwise to a suspension of 60 g (2 mols) of 80% strength sodium hydride in 2,000 ml of absolute dimethylformamide, while cooling and stirring. After one hour at room temperature, 312.9 g (2.1 mols) of dimethylallyl bromide are added dropwise, again at 0° C. The mixture is stirred at room temperature overnight and thereafter the solvent is largely evaporated off and the residue is carefully hydrolyzed. The product is extracted with three 400 mL portions of methylene chloride and the combined organic phases are washed with two 400 ml portions of water. After drying over sodium sulphate and stripping off the solvent, the residue which remains is distilled in vacuo. 334.4 g (88% of theory) of 2-(3-methyl-2-butenyloxy)-benzaldehyde of boiling point 110° C./10 mm Hg are obtained.

The following compounds of the general formula (I) are obtained in a corresponding manner:

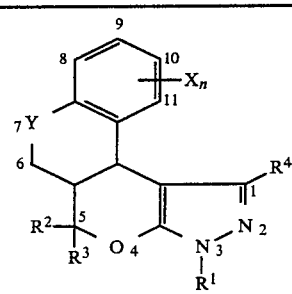

(I)

| Example No. | $R^1$ | $R^2$ | $R^3$ | $R^4$ | X | Y | n | Physical properties [Melting point °C.] |
|---|---|---|---|---|---|---|---|---|
| 2 | C₆H₅— | CH₃ | CH₃ | CH₃ | — | O | 0 | |
| 3 | C₆H₅— | H | H | CH₃ | — | O | 0 | 149–50 |
| 4 | CH₃ | CH₃ | CH₃ | CH₃ | — | O | 0 | 143–45 |
| 5 | 2,6-Cl₂-C₆H₃-CH(CH₃)— | CH₃ | CH₃ | CH₃ | — | O | 0 | 168–70 |
| 6 | H | CH₃ | CH₃ | CH₃ | 9-OCH₃ | O | 1 | >280 |
| 7 | H | CH₃ | CH₃ | CH₃ | 8,10-Cl₂ | O | 2 | >280 |
| 8 | H | CH₃ | CH₃ | CH₃ | 9,10-(OCH₃)₂ | O | 2 | 239–42 |
| 9 | H | CH₃ | CH₃ | CH₃ | 8-OCH₃ | O | 1 | 237 |
| 10 | H | CH₃ | CH₃ | CH₃ | 10-NO₂ | O | 1 | >260 |
| 11 | CH₃—CO— | CH₃ | CH₃ | CH₃ | — | O | 0 | 153–54 |
| 12 | CH₃—CO— | H | H | CH₃ | — | O | 0 | 164–66 |
| 13 | CH₃—CO— | CH₃ | CH₃ | CH₃ | 8,11-Cl₂ | O | 0 | 203 |
| 14 | H | C₆H₅ | H | CH₃ | — | O | 0 | >280 |
| 15 | CH₃—CO— | C₆H₅ | H | CH₃ | — | O | 0 | 183–85 |
| 16 | H | CH₃ | H | CH₃ | — | O | 0 | 199–200 |

-continued

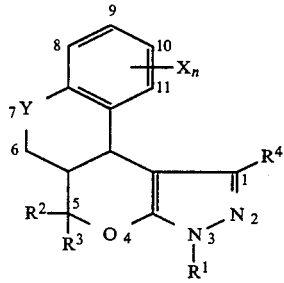

(I)

| Example No. | $R^1$ | $R^2$ | $R^3$ | $R^4$ | X | Y | n | Physical properties [Melting point °C.] |
|---|---|---|---|---|---|---|---|---|
| 17 | H | $CH_3$ | $CH_3$ | $COOC_2H_5$ | — | O | 0 | 128-32 |
| 18 | H | $CH_3$ | $CH_3$ | $CH_3$ | — | S | 0 | 256 |
| 19 | H | $CH_3$ | $CH_3$ | $(CH_3)_3C-$ | — | O | 0 | 238-40 |
| 20 | H | $CH_3$ | $CH_3$ | $C_6H_5$ | — | O | 0 | 235-37 |
| 21 | H | $CH_3$ | $CH_3$ | $(CH_3)_2CH-$ | — | O | 0 | 258-60 |
| 22 | $CH_3-CO$ | $CH_3$ | $CH_3$ | $CH_3$ | — | S | 0 | 142-143 |
| 23 | H | $CH_3$ | $CH_3$ | $CH_3$ | 10-Br | O | 0 | >260 |
| 24 | $C_2H_5O-CO-$ | $CH_3$ | $CH_3$ | $CH_3$ | — | O | 0 | 104 |
| 25 | $CH_3O-CO-$ | $CH_3$ | $CH_3$ | $CH_3$ | — | O | 0 | 171 |
| 26 | H | $CH_3$ | $CH_3$ | $CH_3$ | $9-N(C_2H_5)_2$ | O | 1 | 230(Decomp.) |

USE EXAMPLES

The compound shown below is used as a comparison substance in the use example which follows:

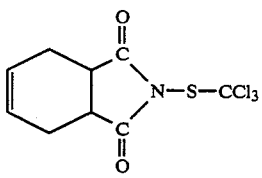

(A)

N-Trichloromethylthio-tetrahydrophthalimide

EXAMPLE A

Botrytis test (beans)/protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compounds according to the following preparation examples: 1, 6, 7, 9, 10 and 11.

It will be understood that the specification and examples are illustrative but not limitative of the present invention and that other embodiments within the spirit and scope of the invention will suggest themselves to those skilled in the art.

We claim:
1. A pyrano-pyrazole derivative of the formula

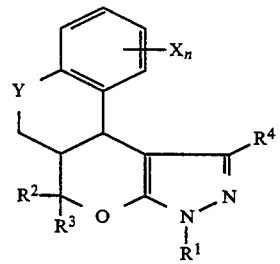

in which
$R^1$ represents hydrogen, straight-chain or branched alkyl, alkanoyl or alkoxycarbonyl with in each case up to 4 carbon atoms in the alkyl part, phenyl which is optionally monosubstituted or polysubstituted by identical or different substituents or phenylalkyl which has 1 or 2 carbon atoms in the alkyl part and is optionally monosubstituted or polysubstituted by identical or different substituents, possible substituents on the phenyl in each case being: halogen, cyano, nitro, alkyl with up to 4 carbon atoms, alkoxy, alkylthio and dialkylamino with 1 or 2 carbon atoms in the particular alkyl parts, and halogenoalkyl with 1 or 2 carbon atoms and up to 5 identical or different halogen atoms,
$R^2$ and $R^3$, which can be identical or different, represent hydrogen, straight-chain or branched alkyl with up to 4 carbon atoms or phenyl which is optionally monosubstituted or polysubstituted by identical or different substituents from the group comprising halogen and alkyl with up to 4 carbon atoms,
$R^4$ represents straight-chain or branched alkyl or alkoxycarbonyl with in each case up to 4 carbon atoms in the alkyl part, cyano or phenyl which is optionally monosubstituted or polysubstituted by identical or different substituents from the group comprising halogen and alkyl with up to 4 carbon atoms, Y represents oxygen, sulphur or the methylene group, X represents halogen, cyano, nitro, straight-chain or branched alkyl with up to 4 carbon atoms, alkoxy, alkylthio or dialkylamino with 1 or 2 carbon atoms in the particular alkyl parts or halogenoalkyl with 1 or 2 carbon atoms and up to 5 identical or different halogen atoms, and n represents a number from 0 to 3.

2. A pyrano-pyrazole derivative according to claim 1, in which

R¹ represents hydrogen, methyl, ethyl or n- or i-propyl, acetyl, methoxycarbonyl or ethoxycarbonyl, or phenyl, benzyl or phenethyl which is optionally mono-, di- or tri-substituted by identical or different substituents, suitable substituents on the particular phenyl being: fluorine, chlorine, bromine, cyano, nitro, methyl, methoxy, methylthio, dimethylamino and trifluoromethyl, R² and R³, which can be identical or different, represent hydrogen, methyl, or phenyl which is optionally mono-, di- or tri-substituted by identical or different substituents from the group comprising chlorine and methyl, R⁴ represents methyl, ethyl, n- or i-propyl, t-butyl, cyano, methoxycarbonyl, ethoxycarbonyl or phenyl which is optionally mono-, di- or trisubstituted by identical or different substituents from the group comprising chlorine and methyl, X represents flourine, chlorine, bromine, cyano, nitro, methyl, methoxy, methylthio, dimethylamino or trifluoromethyl, and n represents a number from 0 to 2.

3. A pyrano-pyrazole according to claim 1 wherein such compound is 1,5,5-trimethyl-5a,11b-dihydro-3H,5H,6H,4,7-dioxa-2,3-diazacyclopenta-[c]-phenanthrene of the formula

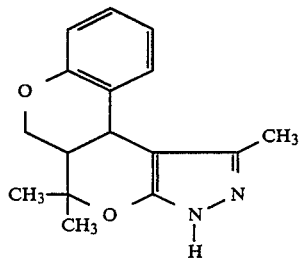

4. A pyrano-pyrazole according to claim 1 wherein such compound is 9-methoxy-1,5,5-trimethyl-5a, 11b-dihydro-3H,5H,6H,4,7-dioxa-2,3-diazacyclopenta-[c]-phenanthrene of the formula

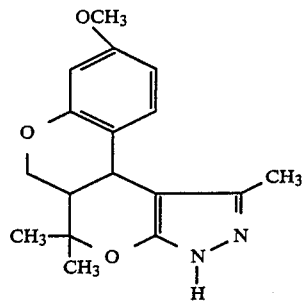

5. A pyrano-pyrazole according to claim 1 wherein such compound is 8-methoxy-1,5,5-trimethyl-5a, 11b-dihydro-3H,5H,6H,4,7-dioxa-2,3-diazacyclopenta-[c]-phenanthrene of the formula

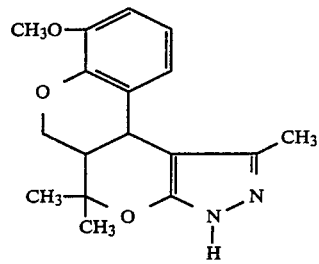

6. A pyrano-pyrazole according to claim 1 wherein such a compound is 10-nitro-1,5,5-trimethyl-5a, 11b-dihydro-3H,5H,6H,4,7-dioxa-2,3-diazacyclopenta-[c]-phenanthrene of the formula

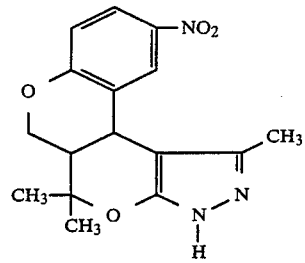

7. A pyrano-pyrazole according to claim 1 wherein such compound is 3-acetyl-1,5,5-trimethyl-5a, 11b-dihydro-3H,5H,6H,4,7-dioxa-2,3-diazacyclopenta-[c]-phenanthrene of the formula

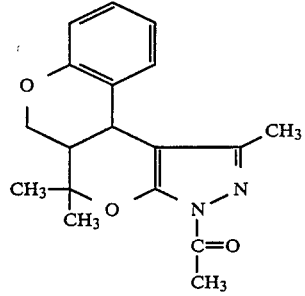

8. A fungicidal composition comprising a fungicidally effective amount of a compound according to claim 1 in admixture with a diluent.

9. A method of combating fungi which comprises applying to such fungi or to a fungus habitat a fungicidally effective amount of a compound according to claim 1.

10. The method according to claim 9, wherein such compound is 1,5,5-trimethyl-5a,11b-dihydro-3H,5H,6H,4,7-dioxa-2,3-diazacyclopenta-[c]-phenanthrene, 9-methoxy-1,5,5-trimethyl-5a,11b-dihydro-3H,5H,6H,4,7-dioxa-2,3-diazacyclopenta-[c]-phenanthrene, 8-methoxy-1,5,5-trimethyl-5a,11b-dihydro-3H,5H,6H,4,7-dioxa-2,3-diazacyclopenta-[c]-phenanthrene, 10-nitro-1,5,5-trimethyl-5a,11b-dihydro-3H,5H,6H,4,7-dioxa-2,3-diazacyclopenta-[c]-phenanthrene or 3-acetyl-1,5,5-trimethyl-5a,11b-dihydro-3H,5H,6H,4,7-dioxa-2,3-diazacyclopenta-[c]-phenanthrene.

* * * * *

UNITED STATES PATENT AND TRADEMARK OFFICE
CERTIFICATE OF CORRECTION

PATENT NO. : 4,515,801
DATED : May 7, 1985
INVENTOR(S) : Hartmut Stegelmeier, et al It is certified that error appears in the above-identified patent and that said Letters Patent is hereby corrected as shown below:

| | |
|---|---|
| Col. 1, line 13 | Delete "Sch/ädlingsbek/ämpfungs-mittel" and substitute --Schädlingsbekämpfungsmittel" |
| Col. 1, lines 38-39 | Correct spelling of "substituted" |
| Col. 1, line 40 | Correct spelling of "optionally" |
| Col. 3, line 4 | Insert space between "4" and --carbon-- |
| Col. 8, line 21 | After "400" delete "mL" and substitute --ml-- |
| Col. 8, line 27 | After "110°C./" delete "10" and substitute --1.0-- |
| Col. 8, Table, Example 2, last column | Insert --152-- |

Signed and Sealed this

Eighth Day of October 1985

[SEAL]

Attest:

DONALD J. QUIGG

Attesting Officer

Commissioner of Patents and Trademarks—Designate